United States Patent

Shoji et al.

[11] Patent Number: 5,480,874
[45] Date of Patent: Jan. 2, 1996

[54] PHOSPHONIC DIESTER DERIVATIVES

[75] Inventors: Yasuo Shoji; Yoshihiko Tsuda, both of Naruto; Kazuhiko Tsutsumi, Tokushima; Yasuhide Inoue, Naruto, all of Japan

[73] Assignee: Otsuka Pharmaceutical Factory, Inc., Tokushima, Japan

[21] Appl. No.: 318,860

[22] PCT Filed: Feb. 10, 1994

[86] PCT No.: PCT/JP94/00209

§ 371 Date: Jan. 12, 1995

§ 102(e) Date: Jan. 12, 1995

[87] PCT Pub. No.: WO94/18212

PCT Pub. Date: Aug. 8, 1994

[30] Foreign Application Priority Data

Feb. 15, 1993 [JP] Japan ................. 5-025732

[51] Int. Cl.⁶ .................. A61K 31/675; C07F 9/28
[52] U.S. Cl. ............. 514/80; 514/81; 514/393; 514/395; 548/113; 548/150; 548/151; 548/302.1
[58] Field of Search ..................... 548/150, 151, 548/302.1, 113; 514/366, 393, 395, 80

[56] References Cited

U.S. PATENT DOCUMENTS

| | | | |
|---|---|---|---|
| 4,232,010 | 11/1980 | Tsukamoto et al. | 424/200 |
| 4,434,162 | 2/1984 | Tsukamoto et al. | 424/200 |
| 4,822,780 | 4/1989 | Tsuda et al. | 514/119 |
| 4,971,957 | 11/1990 | Tsutsumi et al. | 514/79 |
| 5,081,112 | 1/1992 | Tsutsumi et al. | 514/119 |
| 5,376,665 | 12/1994 | Miyata et al. | 514/301 |

FOREIGN PATENT DOCUMENTS

0402033A1  5/1990  European Pat. Off. .

OTHER PUBLICATIONS

Derwent Abstract of JP, A1, 2-11590 (Application No. 163083/88) (1990).
Derwent Abstract of JP, A1, 3-236394 (Application Nos. 344140/89 and 326582/90) (1991).
Derwent Abstract of JP, A1, 4-243888 (Application No. 87143/91) (1992).
Derwent Abstract of JP, A1, 4-244090 (Application No. 418143/90) (1992).
Derwent Abstract of JP, A1, 4-356495 (Application No. 129516/91) (1993).
Derwent Abstract of JP, A1, 5-953 (Application No. 326581/90) (1993).

Primary Examiner—Robert W. Ramsuer
Assistant Examiner—Laura Cross
Attorney, Agent, or Firm—Sughrue, Mion, Zinn, Macpeak & Seas

[57] ABSTRACT

The invention provides a phosphonic diester derivative of the formula:

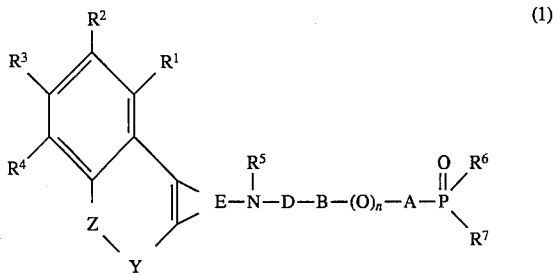

wherein the variables are as defined in the specification. The derivative of the invention has excellent hypolipidemic and hypoglycemic activities and little side effects and hence is useful as therapeutic and prophylactic agents for hyperlipidemic diseases and diabetes and as a therapeutic agent for cataract.

8 Claims, No Drawings

PHOSPHONIC DIESTER DERIVATIVES

This application is a 371 of PCT/JP94/00209 filed Feb. 10, 1994.

TECHNICAL FIELD

The present invention relates to novel phosphonic diester derivatives.

PRIOR ART

The phosphonic diester derivatives of the invention are novel compounds not heretofore described in the literature.

The object of the invention is to provide compounds of value as medicines as will be described hereinafter.

DISCLOSURE OF THE INVENTION

The present invention provides a phosphonic diester derivative of the following general formula (1):

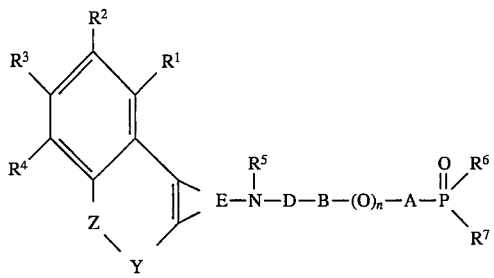

wherein $R^1$, $R^2$, $R^3$ $R^4$ are the same or different and each represents a hydrogen atom, a lower alkyl group, a lower alkoxy group, a halogen-substituted lower alkyl group, a nitro group, a halogen atom, a cyano group, a phenylthio group, a phenylsulfinyl group, a phenylsulfonyl group, a phenyl(lower)alkoxy group, a phenyl(lower)alkylthio group or a benzoyloxy group having a di(lower alkoxy)phosphoryl(lower)alkyl group, and $R^3$ and $R^4$ may jointly represent a group of the formula —CH=CH—CH=CH—; $R^5$ represents a hydrogen atom, a lower alkyl group or a phenyl group; $R^6$ and $R^7$ are the same or different and each represents a lower alkoxy group, a phenyl group or a phenyl(lower)alkoxy group; A represents a lower alkylene group optionally having a phenyl group as a substituent; B represents a benzene ring or thiophene ring; D represents a group of the formula —CO—, a group of the formula —CS— or a group of the formula —SO$_2$—; E represents a group of the formula

a group of the formula

or a group of the formula

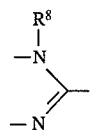

(wherein $R^8$ represents a lower alkyl group); —Z— represents a single bond or —O—; Y represents a lower alkylene group optionally having a phenyl group as a substituent or a vinylene group; and n is an integer of 0 or 1.

Each of the groups relevant to the above general formula (1) includes the following exemplary species.

The lower alkyl group includes straight- or branched-chain lower alkyl groups such as methyl, ethyl, propyl, isopropyl, butyl, isobutyl, tert-butyl, pentyl, hexyl and so on.

The lower alkoxy group includes methoxy, ethoxy, propoxy, butoxy, pentyloxy, hexyloxy and so on.

The halogen-substituted lower alkyl group includes trifluoromethyl, pentafluoroethyl, heptafluoropropyl, nonafluorobutyl, undecafluoropentyl, tridecafluorohexyl and so on.

The halogen atom includes fluorine, chlorine, bromine and iodine.

The lower alkylene group includes methylene, ethylene, trimethylene, tetramethylene, pentamethylene, hexamethylene, methylmethylene, methylethylene, dimethylmethylene and so on.

The lower alkylene group optionally having a phenyl group as a substituent includes the abovementioned lower alkylene groups, phenylmethylene, benzylmethylene, phenylethylene, diphenylmethylene, etc.

The phenyl(lower)alkoxy group includes benzyloxy, 1-phenylethoxy, 2-phenylethoxy, 3-phenylpropoxy, 4-phenylbutoxy, 5-phenylpentyloxy, 6-phenylhexyloxy and so on.

The phenyl(lower)alkylthio group includes benzylthio, 1-phenylethylthio, 2-phenylethylthio, 3-phenylpropylthio, 4-phenylbuthylthio, 5-phenylpentylthio, 6-phenylhexylthio and so on.

The benzoyloxy group having a di(lower alkoxy)phosphoryl(lower)alkyl group includes 4-[(diethoxyphosphoryl)methyl]benzoyloxy, 3-[(diethoxyphosphoryl)methyl]benzoyloxy, 2-[(diethoxyphosphoryl)methyl]benzoyloxy, 4-[(dimethoxyphosphoryl)methyl]benzoyloxy, 4[(dipropoxyphosphoryl)methyl]benzoyloxy, 4-[2-(diethoxyphosphoryl)ethyl]benzoyloxy, 4-[3-(diethoxyphosphoryl)propyl]benzoyloxy and so on.

Among phosphonic diester derivatives of the formula (1) according to the present invention, preferred are those of the formula (1) wherein $R^1$, $R^2$, $R^3$ and $R^4$ are the same or different and each represents a hydrogen atom, a lower alkyl group, a lower alkoxy group, a halogen-substituted lower alkyl group, a halogen atom or a cyano group; $R^5$ represents a hydrogen atom or a lower alkyl group; $R^6$ and $R^7$ each represent a lower alkoxy group; A represents a lower alkylene group; B represents a benzene ring; D represents a group of the formula —CO—; E represents a group of the formula

or a group of the formula

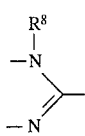

(wherein $R^8$ represents a lower alkyl group); —Z— represents a single bond or —O—; Y represents a lower alkylene group or a vinylene group; and n is 0.

The derivatives of the invention represented by the following formulas (1') and (1") are more preferred.

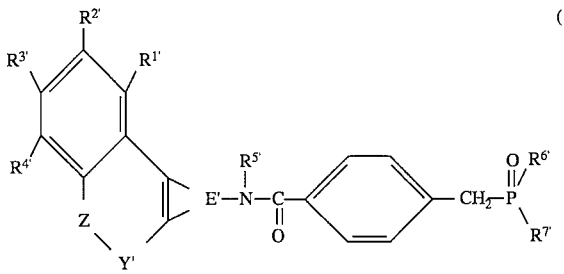 (1')

wherein $R^{1'}$, $R^{2'}$, $R^{3'}$ and $R^{4'}$ are the same or different and each represents a hydrogen atom, a lower alkyl group, a lower alkoxy group, a halogen-substituted lower alkyl group, a halogen atom or a cyano group; $R^{5'}$ represents a hydrogen atom or a lower alkyl group; $R^{6'}$ and $R^{7'}$ each represent a lower alkoxy group; E' represents a group of the formula

group of the formula

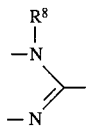

(wherein $R^8$ represents a lower alkyl group); —Z— is as defined above in the formula (1); and Y' represents a lower alkylene group or a vinylene group.

alkyl group; $R^{6''}$ and $R^{7''}$ each represent a lower alkoxy group; E" represents a group of the formula

or a group of the formula

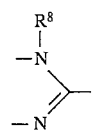

(wherein $R^8$ represents a lower alkyl group); when E" represents the group of

represents a single bond or —O— and and Y" represents a methylene group or a vinylene group, and when E" represents the group of

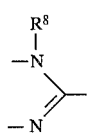

—Z"— represents a single bond and Y" represents a vinylene group.

Specific examples of these preferred derivatives of the invention include:
diethyl 4-[N-(8H-indeno[1,2-d]thiazol-2-yl)carbamoyl]benzylphosphonate,
diethyl 4-[N-(6-chloro-8H-indeno[1,2-d]thiazol-2-yl)carbamoyl]benzylphosphonate,
diethyl 4-[N-(7-chloro-8H-indeno-[1,2-d]thiazol-2-yl)carbamoyl]benzylphosphonate,
diethyl 4-[N-(8-fluoro-4H-[1]benzopyrano[4,3-d]thiazol-2-yl)carbamoyl]benzylphosphonate, and
diethyl 4-[N-(1-methyl-1H-naphtho[1,2-d]imidazole-2yl)carbamoyl]benzylphosphonate.

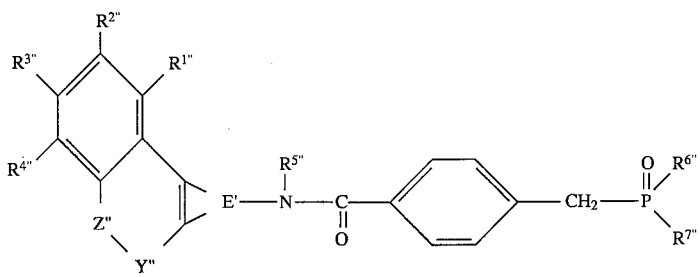 (1")

wherein $R^{1''}$, $R^{2''}$, $R^{3''}$ $R^{4''}$ are the same or different and each represents a hydrogen atom, a lower alkyl group, a lower alkoxy group, a halogen-substituted lower alkyl group or a halogen atom; $R^{5''}$ represents a hydrogen atom or a lower The most preferred derivative of the invention is diethyl 4-[N-(6-chloro-8H-indeno[1,2-d]thiazol-2-yl)carbamoyl] benzylphosphonate.

The phosphonic diester derivative of the formula (1) according to the invention has excellent hypolipidemic and hypoglycemic activities and therapeutic and prophylactic effects on cataract, is hence useful as therapeutic agents for hyperlipidemic diseases, diabetes and cataract and can treat or prevent various types of diseases (hyperlipidemic diseases), e.g. hypercholesterolemia, hypertriglyceridemia, hyperphospholipidemia and hyper-free fatty acidemia, diabetes and cataract. Moreover, the phosphonic diester derivative of the invention has hypotensive activity as well, is hence of value as a hypotensive agent and can treat or prevent hypertension. In addition, the phosphonic diester derivative of the invention has ameliorating and therapeutic effects on cachexia such as cancer cachexia and infectious cachexia and can be used as a therapeutic agent for ameliorating cachexia. Furthermore, the compound of the present invention has little side effects and is hence more advantageous for medical use.

The process for preparing the phosphonic diester derivative according to the invention will be described below in detail. Said compound can be prepared, for example, by the processes shown in the following Reaction Schemata.

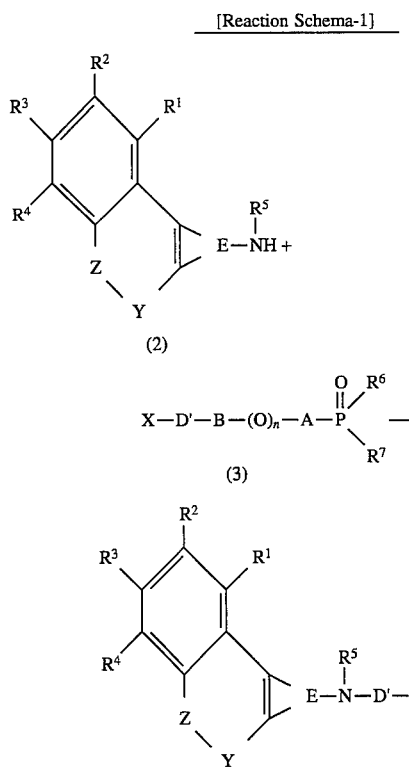

wherein $R^1$, $R^2$, $R^3$, $R^4$, $R^5$, $R^6$, $R^7$, A, B, E, Y, Z and n are as defined hereinbefore, D' represents a group of the formula —CO— or a group of the formula —$SO_2$— and X represents a halogen atom.

According to the process shown in Reaction Schema-1, the compound (1a) of the invention can be prepared by reacting the compound (2) with the acid halogenide (3) in the presence of an acid acceptor in an inert solvent. The inert solvent mentioned above includes, among others, aromatic or aliphatic hydrocarbons such as benzene, toluene, xylene, petroleum ether, etc., acyclic or cyclic ethers such as diethyl ether, 1,2-dimethoxyethane, tetrahydrofuran (THF), 1,4-dioxane, etc., ketones such as acetone, methyl ethyl ketone, acetophenone, etc., and halogenated hydrocarbons such as dichloromethane, chloroform, carbon tetrachloride, 1,2-dichloroethane and so on. Preferable as the acid acceptor is a tertiary amine such as triethylamine and 4-dimethylaminopyridine. The proportions of the compound (2) and the acid halogenide (3) to be used in the above reaction are not critical. The acid halogenide (3) is preferably used in an equimolar to small excess proportion relative to the compound (2). The acid acceptor is preferably used in an equimolar to excess proportion relative to said acid halogenide (3). The reaction can proceed under cooling, at room temperature or under heating but it is usually advantageous to conduct the reaction at 0° C. to the reflux temperature of the solvent. The reaction generally goes-to completion in about 0.5–10 hours.

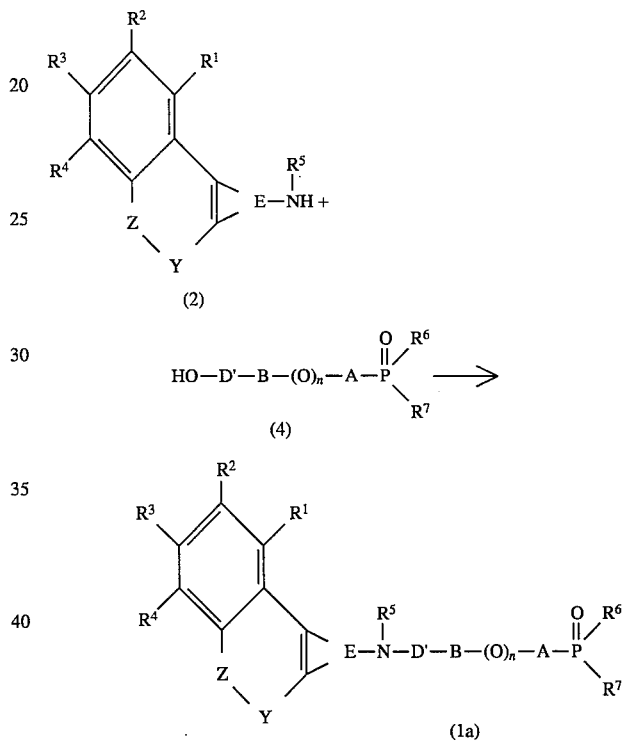

wherein $R^1$, $R^2$, $R^3$, $R^4$, $R^5$, $R^6$, $R^7$, A, B, D', E, Y, Z and n are as defined hereinbefore.

According to the process shown in Reaction Schema-2, the compound (1a) of the invention can be prepared by reacting the compound (2) with the compound (4) in the presence of a condensing agent in an inert solvent. The inert solvent can be any of known aprotic solvents, and N,N-dimethylformamide (DMF) and the like are particularly preferable. The condensing agent includes, for example, N,N-dicyclohexylcarbodiimide (DCC), 1-hydroxybenzotriazole, N-hydroxysuccinimide, diethyl cyanophosphonate, diphenylphosphoryl azide and so on. It is particularly advantageous to employ diethyl cyanophosphonate in combination with triethylamine. The proportions of the compound (2) and the compound (4) to be used in the above reaction are not critical but can be liberally selected from a broad range. It is recommendable to use the compound (4) in an equimolar to small excess proportion, preferably approximately an equimolar proportion, relative to the compound (2). The above condensing agent is used desirably in an equimolar to excess proportion, preferably a small excess, relative to the compound (4). The reaction is conducted under conditions of ice-cooling to room temperature for about 0.5–2 hours.

[Reaction Schema-3]

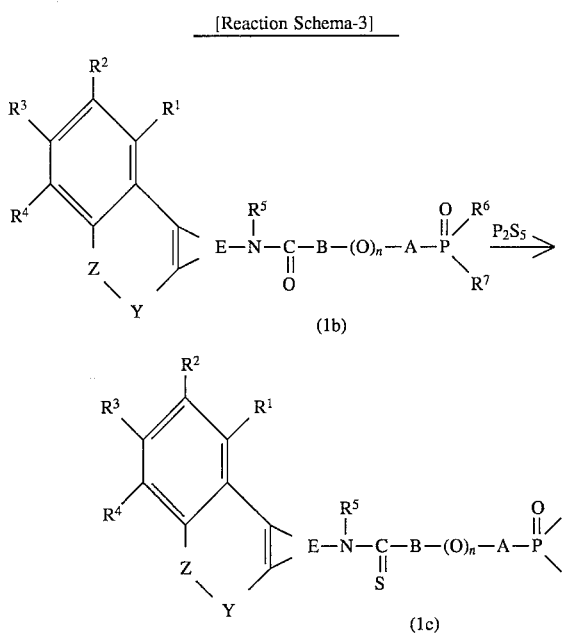

wherein $R^1$, $R^2$, $R^3$, $R^4$, $R^5$, $R^6$, $R^7$, A, B, E, Y, Z and n are as defined above.

The reaction for converting the compound (1b) to the compound (1c) shown in Reaction Schema-3 is carried out by treating the compound (1b) with diphosphorus pentasulfide in an aprotic solvent. Examples of the aprotic solvent are tertiary amines such as pyridine, triethylamine and N,N-dimethylaniline, aromatic hydrocarbons such as benzene, toluene and xylene, and acetonitrile. Among them, a solvent mixture of benzene and pyridine is suitably used. The amount of the diphosphorus pentasulfide used is not critical but can be liberally selected from a broad range. The diphosphorus pentasulfide is generally used in an equimolar to excess proportion relative to the compound (1b), preferably in an amount of about 1.5 to 2.5 moles per mole of the compound (1b). The reaction is generally carried out at room temperature to the reflux temperature of the solvent, preferably at about 70° to 90° C. for about 2–10 hours.

Among the compounds (2) used as the starting compound in Reaction Schemata-1 and -2, compounds of the following formulas (2a) and (2b) can be prepared, for example, by the processes shown below in Reaction Schema-4 and Reaction Schema-5.

[Reaction Schema-4]

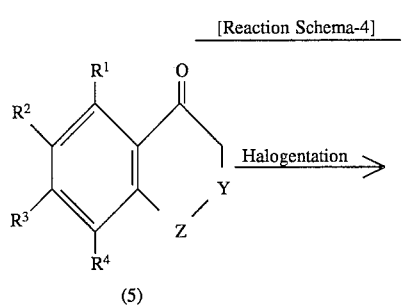

[Reaction Schema-4] -continued

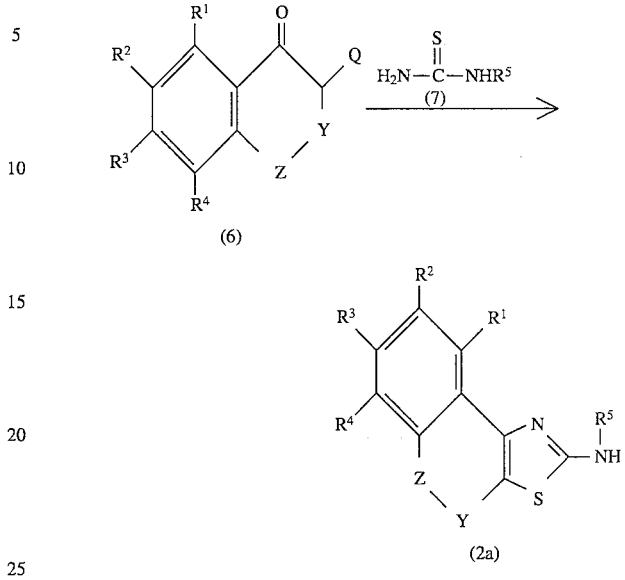

[Reaction Schema-5]

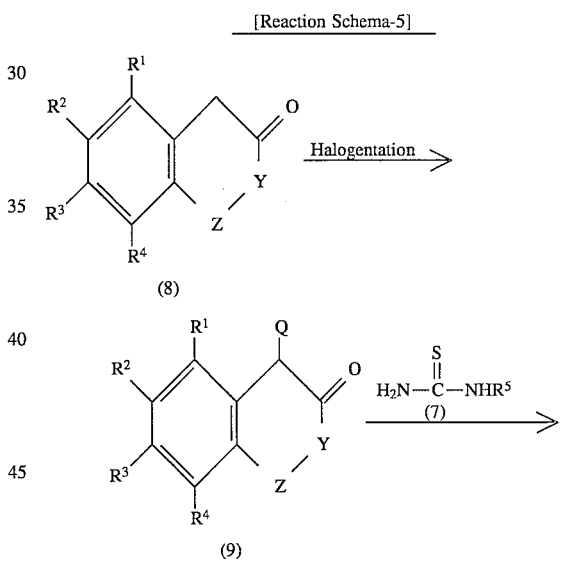

wherein $R^1$, $R^2$, $R^3$, $R^4$, $R^5$, Y and Z are as defined hereinbefore and Q represents a halogen atom.

The halogenation reactions of the compounds (5) and (8) in Reaction Schemata-4 and -5, respectively can be carried out using a halogenating agent in an inert solvent. The inert solvent includes, among others, chloroform, dichloromethane, 1,2-dichloroethane, a solvent mixture of these and a lower alcohol such as methanol and ethanol. The halogenating agent includes phenyltrimethylammonium tribromide, bromine, iodine, etc. When a simple substance of halogen such as bromine and iodine is used as the halogenating agent, the reaction is carried out preferably in the presence of a Lewis acid Lewis acid such as aluminum chloride and boron trifluoride. The halogenating agent is preferably used in an equimolar to small excess proportion relative to the compound (5) or (8). The reaction is carried out under conditions of ice-cooling to room temperature for about 2–5 hours.

The halogenides (6) and (9) obtained by the reaction are reacted with a thiourea derivative (7) for conversion to compounds (2a) and (2b), respectively. The reaction is carried out using the thiourea derivative (7) in approximately an equimolar proportion relative to the halogenides (6) and (9) in an inert solvent, e.g. ethanol, methanol, ethylene glycol, water, etc., at about 110°–130° C. for about 1–3 hours, Among the starting compounds (2), the compounds of the following formulas (2c) and (2d) can be prepared, for example, by the process shown below in Reaction Schema-6.

(10). The reaction is carried out at room temperature to the reflux temperature of the solvent for about 1–24 hours.

The contemplated compound (2d) can be obtained by reacting the compound (10) with the compound (12) and subjecting the resultant compound (13) to cyclization reaction.

The reaction of the compound (10) with the compound (12) can be carried out using these compounds in approximately equal amounts in an inert solvent such as methanol, ethanol, acetonitrile, dimethylformamide, pyridine, etc. at room temperature to approximately the boiling point of the solvent for about 1–10 hours, thus giving the compound (13).

The cyclization reaction of the compound (13) can be carried out in the presence of a cyclizing agent in an amount of 3 to 5 equivalents in an inert solvent such as dichloromethane, chloroform, 1,2-dichloroethane, etc. Mercury chloride (II), mercury acetate (II), mercury oxide (II), etc. are preferably used as the cyclizing agent. The cyclization reaction is carried out at room temperature to the reflux temperature of the solvent for about 1–20 hours.

The objective compound in each of the above processes can be easily isolated and purified by conventional separation procedures. Such procedures include adsorption chro-

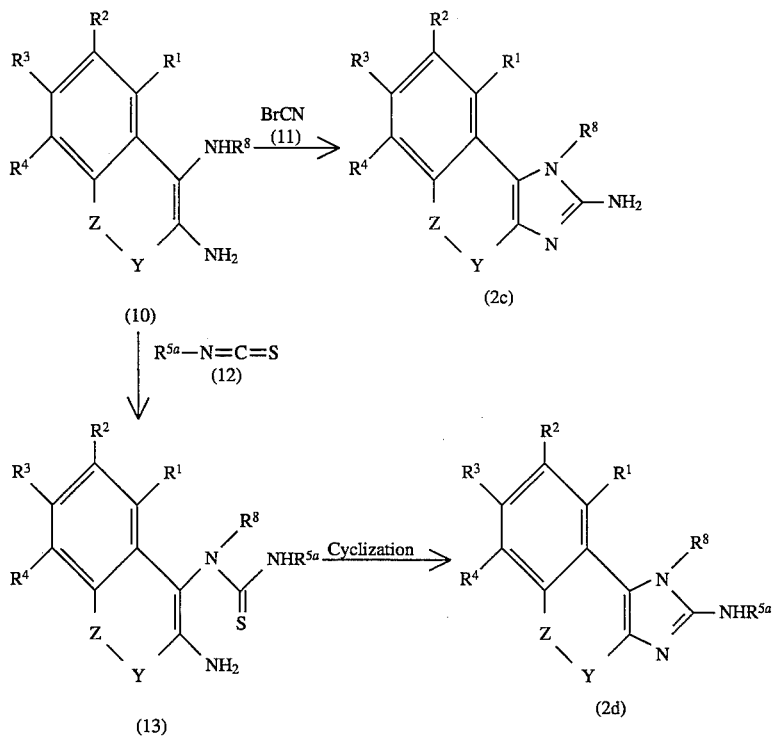

wherein $R^1$, $R^2$, $R^3$, $R^4$, $R^8$, Y and Z are as defined hereinbefore and $R5^a$ represents a lower alkyl group or a phenyl group.

According to the process shown in Reaction Schema-6, the objective compound (2c) can be obtained by reacting the compound (10) with the compound (11) in an inert solvent such as methanol, ethanol, water, acetonitrile and an ethanol/water mixture. The compound (11) is used preferably in an equimolar to excess proportion relative to the compound matography, preparative thin-layer chromatography, solvent extraction, recrystallization and so on.

Among the compounds according to the invention, some may exist as optical isomers, which, of course, are subsumed in the concept of the compound of the invention. The above optical isomers can be easily fractionated by conventional resolution procedures such as those using a reagent for optical resolution.

Using suitable pharmaceutically acceptable carriers, the compound of the invention is made into pharmaceutical compositions for use. Useful pharmaceutically acceptable carriers include various conventional diluents or excipients such as fillers, volume builders, binders, humectants, disintegrators, surfactants, lubricants, etc. and are selectively employed according to the desired unit dosage form.

The above pharmaceutical composition can be provided in a variety of unit dosage forms according to the intended medical treatment. Typical examples are tablets, pills, powders, solutions, suspensions, emulsions, granules, capsules, suppositories, injections (solutions, suspensions, etc.) and ointments.

The molding of tablets can be made using, as said pharmaceutically acceptable carriers, an excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose syrup, starch solution, gelatin solution, carboxymethylcellulose, hydroxypropyl cellulose, methylcellulose, polyvinylpyrrolidone, etc., a disintegrator such as carboxymethyl cellulose sodium, carboxymethylcellulose calcium, low-substituted hydroxypropyl cellulose, dry starch, sodium alginate, agar powder, laminaran powder, sodium hydrogen carbonate, calcium carbonate, etc., a surfactant such as polyoxyethylene sorbitan fatty acid ester, sodium lauryl sulfate, stearyl monoglyceride, etc., a disintegration inhibitor such as sucrose, stearin, cacao butter, hydrogenated oil, etc., an absorption promoter such as quaternary ammonium bases, sodium lauryl sulfate, etc., a humectant such as glycerin, starch, etc., an adsorbent such as starch, lactose, kaolin, bentonite, colloidal silica, etc., and a lubricant such as purified talc, salts of stearic acid, boric acid powder, polyethylene glycol and so on. Furthermore, such tablets can be coated, if necessary, to provide sugar-coated tablets, gelatin-coated tablets, enteric tablets, film-coated tablets, etc. or be processed into double-layer or multiple-layer tablets.

In the manufacture of pills, various excipients such as glucose, lactose, starch, cacao butter, hydrogenated vegetable oil, kaolin, talc, etc., binders such as gum arabic powder, gum tragacanth powder, gelatin, ethanol, etc. and disintegrators such as laminaran, starch, etc. can be employed as the pharmaceutically acceptable carrier.

The suppositories can be manufactured using polyethylene glycol, cacao butter, higher alcohols or their esters, gelatin, semisynthetic glycerides, etc. as the carrier.

The capsules can be manufactured in the conventional manner by blending the compound of the invention with any of the various pharmaceutically acceptable carriers mentioned above and filling the resulting composition into hard gelatin capsule shells, soft capsule shells or the like.

When the compound of the invention is to be provided in an injectable form such as a solution, emulsion or suspension, the preparation is preferably sterilized and rendered isotonic with respect to the blood. As the diluent for use in such a preparation, water, ethyl alcohol, macrogols, propylene glycol, ethoxylated isostearyl alcohol, polyoxy-isostearyl alcohol, polyoxyethylene sorbitan fatty acid esters, etc. can be employed. In this operation, sodium chloride, glucose or glycerin may be added to the composition in a sufficient amount to provide an isotonic solution. Conventional solubilizers, buffers, local anesthetics, etc. can also be added.

Further, coloring agents, preservatives, perfumes, flavors, sweeteners, or other pharmacologically active substances can be optionally incorporated in the compositions in the various dosage forms mentioned above.

There is no particular limitation on the treatment regimen for the pharmaceutical composition of the invention. Thus, the proper regimen can be determined according to the particular dosage form, patient's age, sex and other characteristics, severity of disease and other conditions. For example, said tablets, pills, solutions, suspensions, emulsions, granules and capsules are administered by the oral route. The injections are administered singly or in admixture with conventional glucose, amino acid or other infusions by the intravenous route or, if necessary, administered singly by the intramuscular, intradermal, subcutaneous or intraperitoneal route. The suppositories are administered intrarectally.

The proportion of the compound of the formula (1) of the invention in the pharmaceutical composition is not critical but can be liberally selected from a broad range. It is generally preferable that the compound accounts for about 1 to 70 weight % of the final composition. The dosing amount of the pharmaceutical composition can be selected according to the selected regimen, patient's age, sex and other characteristics, severity of disease and other conditions. The dosage of the compound of the invention as the active ingredient is preferably about 0.05–100 mg per kg body weight a day and this amount can be administered in 1 to 4 divided doses.

BEST MODE FOR PRACTICING THE INVENTION

Examples are given below to clarify the invention in more detail. Among the examples, Reference Examples are directed to the preparation of starting compounds for the preparation of the present compounds, Examples are directed to the preparation of the present compounds, and Pharmacological Test Example indicates a test conducted on the present compounds.

Reference Example 1

Preparation of 2-amino-8H-indeno[1,2-d]thiazol(hydrobromide)

A 6.61 g quantity of 1-indanone was dissolved in a solvent mixture of 80 ml of chloroform and 20 ml of methanol. A 20.35 g quantity of phenyltrimethyl ammonium tribromide was added to the solution with stirring at room temperature. The stirring was continued at room temperature for 5 hours, after which the reaction mixture was diluted with 100 ml of water and extracted with chloroform. The chloroform layer was dried over anhydrous sodium sulfate and the solvent was distilled off under reduced pressure. The residue was dissolved in 100 ml of ethanol, 3.81 g of thiourea was added thereto and the mixture was refluxed with heating for 2 hours. The reaction mixture was allowed to cool to room temperature and the precipitate was collected by filtration. The crude crystals obtained were recrystallized from ethanol-n-hexane to provide 7.03 g of the objective compound (melting point: 257°–260° C.). The structure of the obtained compound (compound 1a) is shown in Table 1.

References Examples 2–32

The compounds set forth as compounds 2a–32a in Table 1 were prepared in the same manner as in Reference Example 1. The structures of these compounds are also shown in Table 1.

References Examples 33–53

The compounds set forth as compounds 33a–53a in Table 1 were prepared in the same manner as in Reference Example 1. The structures of these compounds are also shown in Table 1.

TABLE 1

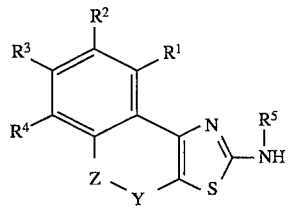

Ph = Phenyl group

| Compound | $R^1$ | $R^2$ | $R^3$ | $R^4$ | $R^5$ | —X— | Y |
|---|---|---|---|---|---|---|---|
| 1a | H | H | H | H | H | Single bond | —CH$_2$— |
| 2a | H | CH$_3$ | H | H | H | Single bond | —CH$_2$— |
| 3a | H | C$_2$H$_5$ | H | H | H | Single bond | —CH$_2$— |
| 4a | H | OCH$_3$ | H | H | H | Single bond | —CH$_2$— |
| 5a | H | F | H | H | H | Single bond | —CH$_2$— |
| 6a | H | Cl | H | H | H | Single bond | —CH$_2$— |
| 7a | H | Br | H | H | H | Single bond | —CH$_2$— |
| 8a | H | H | OCH$_3$ | H | H | Single bond | —CH$_2$— |
| 9a | H | H | F | H | H | Single bond | —CH$_2$— |
| 10a | H | H | Cl | H | H | Single bond | —CH$_2$— |
| 11a | H | H | Br | H | H | Single bond | —CH$_2$— |
| 12a | H | H | H | CH$_3$ | H | Single bond | —CH$_2$— |
| 13a | H | H | H | Cl | H | Single bond | —CH$_2$— |
| 14a | H | H | H | CF$_3$ | H | Single bond | —CH$_2$— |
| 15a | H | OCH$_3$ | OCH$_3$ | H | H | Single bond | —CH$_2$— |
| 16a | OCH$_3$ | OCH$_3$ | OCH$_3$ | H | H | Single bond | —CH$_2$— |
| 17a | OCH$_3$ | OCH$_3$ | OCH$_3$ | Br | H | Single bond | —CH$_2$— |
| 18a | H | H | H | H | H | Single bond | —CH—<br>\|<br>Ph |
| 19a | H | H | H | H | H | Single bond | —C$_2$H$_4$— |
| 20a | H | OCH$_3$ | H | H | H | Single bond | —C$_2$H$_4$— |
| 21a | H | NO$_2$ | H | H | H | Single bond | —C$_2$H$_4$— |
| 22a | H | H | OCH$_3$ | H | H | Single bond | —C$_2$H$_4$— |
| 23a | H | H | H | OCH$_3$ | H | Single bond | —C$_2$H$_4$— |
| 24a | H | CH$_3$ | H | CH$_3$ | H | Single bond | —C$_2$H$_4$— |
| 25a | H | H | H | H | H | Single bond | —CH—CH$_2$—<br>\|<br>CH$_3$ |
| 26a | H | H | H | H | H | Single bond | —CH$_2$— |
| 27a | H | F | H | H | H | Single bond | —CH$_2$— |
| 28a | H | Cl | H | H | H | Single bond | —CH$_2$— |
| 29a | H | F | H | H | H | —O— | —CH—<br>\|<br>CH$_3$ |

TABLE 1-continued

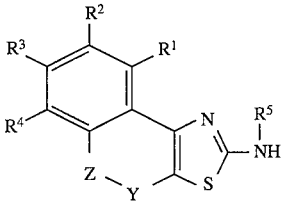

Ph = Phenyl group

| Compound | R¹ | R² | R³ | R⁴ | R⁵ | —X— | Y |
|---|---|---|---|---|---|---|---|
| 30a | H | H | H | H | H | —O— | —CH—<br>\|<br>Ph |
| 31a | H | H | Cl | H | Ph | Single bond | —CH₂— |
| 32a | H | H | Cl | H | CH₃ | Single bond | —CH₂— |
| 33a | CH₃ | H | H | H | H | Single bond | —CH₂— |
| 34a | OCH₃ | H | H | H | H | Single bond | —CH₂— |
| 35a | H | H | CH₃ | H | H | Single bond | —CH₂— |
| 36a | H | H | Cl | H | C₂H₅ | Single bond | —CH₂— |
| 37a | H | H | CN | H | H | Single bond | —CH₂— |
| 38a | H | H | SPh | H | H | Single bond | —CH₂— |
| 39a | H | H | SOPh | H | H | Single bond | —CH₂— |
| 40a | H | H | SO₂Ph | H | H | Single bond | —CH₂— |
| 41a | H | H | SCH₂Ph | H | H | Single bond | —CH₂— |
| 42a | H | H | H | —OCH₃ | H | Single bond | —CH₂— |
| 43a | H | H | H | —O<br>\|<br>CH₂<br>\|<br>Ph | H | Single bond | —CH₂— |
| 44a | H | H | H | Br | H | Single bond | —CH₂— |
| 45a | H | H | H | 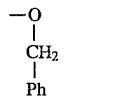 | H | Single bond | —CH₂— |
| 46a | H | H | H | CN | H | Single bond | —CH₂— |
| 47a | H | H | H | F | H | Single bond | —CH₂— |
| 48a | H | H | H | —O<br>\|<br>CH₂<br>\|<br>Ph | H | Single bond | —C₂H₄— |
| 49a | H | H | H | H | H | Single bond | —CH=CH— |
| 50a | H | H | H | H | H | Single bond | —C₃H₆— |

TABLE 1-continued

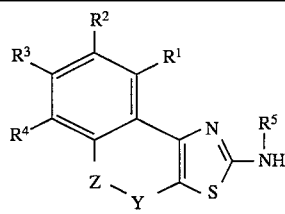

Ph = Phenyl group

| Compound | R¹ | R² | R³ | R⁴ | R⁵ | —X— | Y |
|---|---|---|---|---|---|---|---|
| 51a | H | H | H | H | H | Single bond | —C₃H₆— |
| 52a | H | H | H | Cl | H | —O— | —CH₂— |
| 53a | H | H | H | NO₂ | H | —O— | —CH₂— |

Example 1

Preparation of diethyl 4-[N-(8H-indeno[1,2-d]thiazol-2yl)carbamoyl]benzylphosphonate A 3.76 g portion of the compound 1a and 10 ml of pyridine were dissolved in 30 ml of dry dichloromethane. While the solution was stirred under ice-cooling, a solution of 5.81 g of 4-[(diethoxyphosphoryl)methyl]benzoyl chloride in 10 ml of dry dichloromethane was slowly added dropwise. The stirring was continued at room temperature for 10 hours, after which the reaction mixture was diluted with 30 ml of 10% aqueous sodium hydrogencarbonate solution and extracted with chloroform. The chloroform layer was washed serially with 30 ml of 10% hydrochloric acid and 30 ml of water and dried over anhydrous sodium sulfate. The solvent was distilled off under reduced pressure. The residue was subjected to silica gel column chromatography (eluent: chloroform: ethyl acetate=1:10) and the resulting crude crystals were recrystallized from ethanol-n-hexane to provide 3.79 g of the objective compound as colorless crystals. The structure and the melting point of the compound thus obtained (compound 1) are shown in Table 2.

Examples 2–35

The compounds set forth as compounds 2 to 35 in Table 2 were prepared in the same manner as in Example 1. The structures and melting points of these compounds are also shown in Table 2.

Examples 36–66

The compounds set forth as compounds 36 to 66 in Table 2 were prepared in the same manner as in Example 1. The structures and melting points of these compounds are also shown in Table 2.

TABLE 2

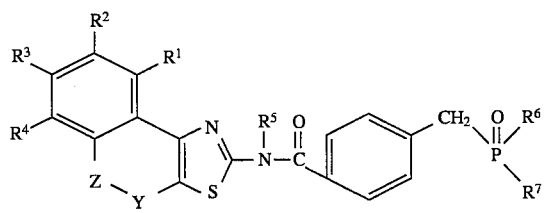

Ph = Phenyl group

| Compound | R¹ | R² | R³ | R⁴ | R⁵ | R⁶=R⁷ | Z | Y | Mp (°C.) |
|---|---|---|---|---|---|---|---|---|---|
| 1 | H | H | H | H | H | OC₂H₅ | Single bond | —CH₂— | 191–193 (Ethanol-n-hexane) |
| 2 | H | H | H | H | H | OCH₃ | Single bond | —CH₂— | 198–200 (Ethanol-n-hexane) |
| 3 | H | H | H | H | H | OCH(CH₃)₂ | Single bond | —CH₂— | 191–193 (Ethanol-n-hexane) |
| 4 | H | CH₃ | H | H | H | OC₂H₅ | Single bond | —CH₂— | 220–222 (Ethanol-n-hexane) |
| 5 | H | C₂H₅ | H | H | H | OC₂H₅ | Single bond | —CH₂— | 226–228 (Ethanol-n-hexane) |
| 6 | H | OCH₃ | H | H | H | OC₂H₅ | Single | —CH₂— | 217–219 |

TABLE 2-continued

Ph = Phenyl group

| Compound | R¹ | R² | R³ | R⁴ | R⁵ | R⁶=R⁷ | Z | Y | Mp (°C.) |
|---|---|---|---|---|---|---|---|---|---|
| 7 | H | F | H | H | H | $OC_2H_5$ | Single bond | $-CH_2-$ | 205–206 (Ethanol-n-hexane) |
| 8 | H | Cl | H | H | H | $OC_2H_5$ | Single bond | $-CH_2-$ | 198–200 (Ethanol-n-hexane) |
| 9 | H | Br | H | H | H | $OC_2H_5$ | Single bond | $-CH_2-$ | 209–210 (Ethanol-n-hexane) |
| 10 | H | H | $OCH_3$ | H | H | $OC_2H_5$ | Single bond | $-CH_2-$ | 198–200 (Ethanol-n-hexane) |
| 11 | H | H | F | H | H | $OC_2H_5$ | Single bond | $-CH_2-$ | 216–218 (Ethanol-n-hexane) |
| 12 | H | H | Cl | H | H | $OC_2H_5$ | Single bond | $-CH_2-$ | 222–224 (Ethanol-n-hexane) |
| 13 | H | H | Br | H | H | $OC_2H_5$ | Single bond | $-CH_2-$ | 224–226 (Ethanol-n-hexane) |
| 14 | H | H | H | $CH_3$ | H | $OC_2H_5$ | Single bond | $-CH_2-$ | 235–237 (Ethanol-n-hexane) |
| 15 | H | H | H | Cl | H | $OC_2H_5$ | Single bond | $-CH_2-$ | 231–233 (Ethanol-n-hexane) |
| 16 | H | H | H | $CF_3$ | H | $OC_2H_5$ | Single bond | $-CH_2-$ | 216–218 (Ethanol-n-hexane) |
| 17 | H | $OCH_3$ | $OCH_3$ | H | H | $OC_2H_5$ | Single bond | $-CH_2-$ | 218–220 (Ethyl acetate-n-hexane) |
| 18 | $OCH_3$ | $OCH_3$ | $OCH_3$ | H | H | $OC_2H_5$ | Single bond | $-CH_2-$ | 194–196 (Ethanol-n-hexane) |
| 19 | $OCH_3$ | $OCH_3$ | $OCH_3$ | Br | H | $OC_2H_5$ | Single bond | $-CH_2-$ | 217–219 (Ethanol-n-hexane) |
| 20 | H | H | H | H | H | $OC_2H_5$ | Single bond | $-CH-$<br>$\|$<br>Ph | 170–173 (Ethyl acetate-n-hexane) |
| 21 | H | H | H | H | H | $OC_2H_5$ | Single bond | $-C_2H_4-$ | 158–160 (Ethanol-n-hexane) |
| 22 | H | H | H | H | H | $CH_3$<br>$\|$<br>$OCH$<br>$\|$<br>$CH_3$ | Single bond | $-C_2H_4-$ | 202–204 (Ethyl acetate n-hexane) |
| 23 | H | $OCH_3$ | H | H | H | $OC_2H_5$ | Single bond | $-C_2H_4-$ | 152.5–154.5 (Ethanol-n-hexane) |
| 24 | H | $NO_2$ | H | H | H | $OC_2H_5$ | Single bond | $-C_2H_4-$ | 243–245 (Ethanol-n-hexane) |
| 25 | H | H | $OCH_3$ | H | H | $OC_2H_5$ | Single bond | $-C_2H_4-$ | 175–177 (Ethanol-n-hexane) |
| 26 | H | H | H | $OCH_3$ | H | $OC_2H_5$ | Single | $-C_2H_4-$ | 187–189 |

TABLE 2-continued

Ph = Phenyl group

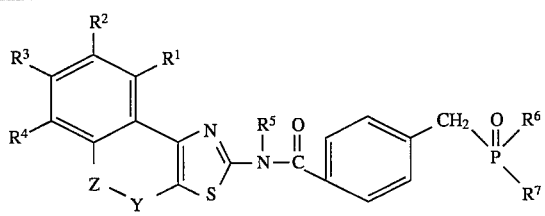

| Compound | R¹ | R² | R³ | R⁴ | R⁵ | R⁶=R⁷ | Z | Y | Mp (°C.) |
|---|---|---|---|---|---|---|---|---|---|
| 27 | H | CH₃ | H | CH₃ | H | OC₂H₅ | Single bond | —C₂H₄— | 215–217 (Ethanol-n-hexane) |
| 28 | H | H | H | H | H | OC₂H₅ | Single bond | —CH—CH₂—<br>\|<br>CH₃ | 164.5–166.5 (Ethanol-n-hexane) |
| 29 | H | H | H | H | H | OC₂H₅ | O bond | —CH₂— | 174–176 (Ethanol-n-hexane) |
| 30 | H | F | H | H | H | OC₂H₅ | O bond | —CH₂— | 165–167 (Ethanol-n-hexane) |
| 31 | H | Cl | H | H | H | OC₂H₅ | O bond | —CH₂— | 204–206 (Ethanol-n-hexane) |
| 32 | H | F | H | H | H | OC₂H₅ | O | —CH—<br>\|<br>CH₃ | 160–162 (Ethyl acetate-n-hexane |
| 33 | H | H | H | H | H | OC₂H₅ | O | —CH—<br>\|<br>Ph | 165–167 (Ethyl acetate-n-hexane) |
| 34 | H | H | Cl | H | Ph | OC₂H₅ | Single bond | —CH₂— | 123–125 (Ethyl acetate-n-hexane) |
| 35 | H | H | Cl | H | CH₃ | OC₂H₅ | Single bond | —CH₂— | 155–157 (Ethanol-n-hexane) |
| 36 | CH₃ | H | H | H | H | OCH₃ | Single bond | —CH₂— | 208–211 (Ethanol-n-hexane) |
| 37 | CH₃ | H | H | H | H | OC₂H₅ | Single bond | —CH₂— | 185–187 (Ethanol-n-hexane) |
| 38 | OCH₃ | H | H | H | H | OC₂H₅ | Single bond | —CH₂— | 211–213 (Ethanol-n-hexane) |
| 39 | H | H | CH₃ | H | H | OC₂H₅ | Single bond | —CH₂— | 206–208 (Ethanol-n-hexane) |
| 40 | H | H | Cl | H | H | OCH₃ | Single bond | —CH₂— | 223–225 (Ethanol-n-hexane) |
| 41 | H | H | Cl | H | C₂H₅ | OC₂H₅ | Single bond | —CH₂— | 88–90 (Ethyl acetate-n-hexane) |
| 42 | H | H | Cl | H | H | OCH(CH₃)₂ | Single bond | —CH₂— | 221–223 (Ethanol-n-hexane) |
| 43 | H | H | Cl | H | H | O(CH₂)₂CH₃ | Single bond | —CH₂— | 165–167 (Ethyl acetate n-hexane) |
| 44 | H | H | CN | H | H | OC₂H₅ | Single bond | —CH₂— | 245–247 (Ethanol-n-hexane) |
| 45 | H | H | SPh | H | H | OC₂H₅ | Single bond | —CH₂— | 182–183 (Ethanol-n-hexane) |
| 46 | H | H | SOPh | H | H | OC₂H₅ | Single | —CH₂— | 161–163 |

TABLE 2-continued

Ph = Phenyl group

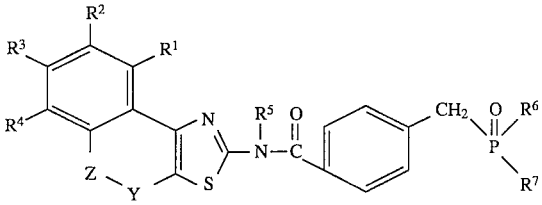

| Compound | R¹ | R² | R³ | R⁴ | R⁵ | R⁶=R⁷ | Z | Y | Mp (°C.) |
|---|---|---|---|---|---|---|---|---|---|
| 47 | H | H | SO$_2$Ph | H | H | OC$_2$H$_5$ | Single bond | —CH$_2$— | 229–231 (Ethanol-n-hexane) |
| 48 | H | H | SCH$_2$Ph | H | H | OC$_2$H$_5$ | Single bond | —CH$_2$— | 163–165 (Ethanol-n-hexane) |
| 49 | H | H | H | OCH$_3$ | H | OC$_2$H$_5$ | Single bond | —CH$_2$— | 224–225 (Ethanol-n-hexane) |
| 50 | H | H | H | OCH$_2$Ph | H | OC$_2$H$_5$ | Single bond | —CH$_2$— | 180–182 (Ethanol-n-hexane) |
| 51 | H | H | H | 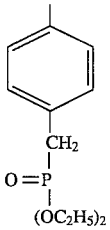 | H | OC$_2$H$_5$ | Single bond | —CH$_2$— | 151–153 (Ethyl acetate-n-hexane) |
| 52 | H | H | H | Br | H | OC$_2$H$_5$ | Single bond | —CH$_2$— | 223–224 (Ethanol-n-hexane) |
| 53 | H | H | H | CN | H | OC$_2$H$_5$ | Single bond | —CH$_2$— | 248–240 (Ethanol-n-hexane) |
| 54 | H | H | H | H | H | OCH$_3$ | Single bond | —C$_2$H$_4$— | 183–186 (Ethanol-n-hexane) |
| 55 | H | H | H | OCH$_2$Ph | H | OC$_2$H$_5$ | Single bond | —C$_2$H$_4$— | 201–203 (Ethanol-n-hexane) |
| 56 | H | H | H | H | H | OC$_2$H$_5$ | Single bond | —CH=CH— | 182–184 (Ethanol-n-hexane) |
| 57 | H | H | H | H | H | OCH$_3$ | Single bond | —C$_3$H$_6$— | 216–218 (Ethanol-n-hexane) |
| 58 | H | H | H | H | H | OC$_2$H$_5$ | Single bond | —C$_3$H$_6$— | 181–183 (Ethanol-n-hexane) |
| 59 | H | H | H | H | H | OCH(CH$_3$)$_2$ | Single bond | —C$_3$H$_6$— | 169–171 (Ethyl acetate-n-hexane) |
| 60 | H | F | H | H | H | OC$_2$H$_5$ | Single bond | —C$_3$H$_6$— | 208–210 (Ethanol-n-hexane) |
| 61 | H | F | H | H | H | OCH$_3$ | —O— | —CH$_2$— | 203–205 (Ethanol-n-hexane) |
| 62 | H | F | H | H | H | OCH(CH$_3$)$_2$ | —O— | —CH$_2$— | 173–175 (Ethanol-n-hexane) |
| 63 | H | H | H | Cl | H | OC$_2$H$_5$ | —O— | —CH$_2$— | 194–196 (Ethanol-n-hexane) |
| 64 | H | H | H | NO$_2$ | H | OC$_2$H$_5$ | —O— | —CH$_2$— | 247–250 (Ethanol- |

TABLE 2-continued

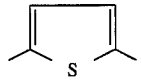

Ph = Phenyl group

| Compound | R¹ | R² | R³ | R⁴ | R⁵ | R⁶=R⁷ | Z | Y | Mp (°C.) |
|---|---|---|---|---|---|---|---|---|---|
| 65 | H | H | H | F | H | OC₂H₅ | Single bond | —CH₂— | 231–233 (Ethanol-n-hexane) |
| 66 | H | H | —CH=CH—CH=CH— | | H | OC₂H₅ | Single bond | —C₂H₄— | 205 (Dec.) (Chloroform-n-hexane) |

Examples 67–82

The compounds set forth as compounds 67 to 82 in Table 3 were prepared in the same manner as in Example 1. The structures and melting points of these compounds are also shown in Table 3.

TABLE 3

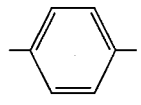

Ph = Phenyl group

| Compound | R¹ | R² | R³ | R⁴ | R⁵ | R⁶ | R⁷ | B | Z | Y | A | n | Mp (°C.) |
|---|---|---|---|---|---|---|---|---|---|---|---|---|---|
| 67 | H | H | Cl | H | H | OC₂H₅ | OC₂H₅ | 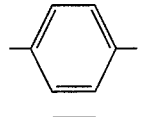 | Single bond | —CH₂— | —CH₂— | 0 | 223–225 (Ethanol-n-hexane) |
| 68 | H | H | Cl | H | H | OC₂H₅ | OC₂H₅ | 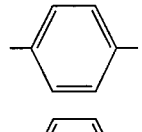 | Single bond | —CH₂— | —CH—<br>\|<br>CH₃ | 0 | 220–222 (Ethanol-n-hexane) |
| 69 | H | H | Cl | H | H | OC₂H₅ | OC₂H₅ |  | Single bond | —CH₂— | —CH—<br>\|<br>CH₂—Ph | 0 | 235–237 (Ethyl acetate-n-hexane) |
| 70 | H | H | Cl | H | H | OC₂H₅ | OC₂H₅ |  | Single bond | —CH₂— | —C₂H₄— | 1 | 166–168 (Ethanol-n-hexane) |
| 71 | H | H | Cl | H | H | OC₂H₅ | OC₂H₅ |  | Single bond | —CH₂— | —C₃H₆— | 1 | 201–203 (Ethanol) |

TABLE 3-continued

Ph = Phenyl group

| Compound | R¹ | R² | R³ | R⁴ | R⁵ | R⁶ | R⁷ | B | Z | Y | A | n | Mp (°C.) |
|---|---|---|---|---|---|---|---|---|---|---|---|---|---|
| 72 | H | H | Cl | H | H | $OC_2H_5$ | $\begin{array}{c}CH_3\\|\\OCH\\|\\CH_3\end{array}$ | 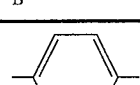 | Single bond | $-CH_2-$ | $-CH_2-$ | 0 | 218–220 (Ethanol-n-hexane) |
| 73 | H | H | Cl | H | H | $OCH_2H_5$ | $OCH_2Ph$ | 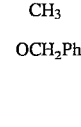 | Single bond | $-CH_2-$ | $-CH_2-$ | 0 | 89–92 (Ethyl acetate-n-hexane) |
| 74 | H | H | Cl | H | H | $OCH_2H_5$ | Ph | 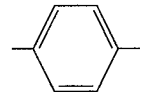 | Single bond | $-CH_2-$ | $-CH_2-$ | 0 | 250–252 (Ethanol-n-hexane) |
| 75 | H | H | H | Cl | H | $OCH_2H_5$ | $OC_2H_5$ | 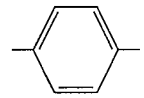 | Single bond | $-CH_2-$ | $-CH_2-$ | 0 | 240–242 (Ethanol-n-hexane) |
| 76 | H | F | Cl | H | H | $OCH_2H_5$ | $OC_2H_5$ | 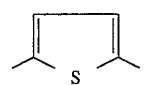 | Single bond | $-C_3H_6-$ | $-CH_2-$ | 0 | 185–187 (Ethanol-n-hexane) |
| 77 | H | F | Cl | H | H | $OCH_2H_5$ | $OC_2H_5$ | 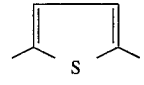 | $-O-$ | $-CH_2-$ | $-CH_2-$ | 0 | 190–192 (Ethanol-n-hexane) |
| 78 | H | F | Cl | H | H | $OCH_2H_5$ | $OC_2H_5$ | 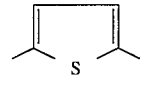 | $-O-$ | $-CH_2-$ | $\begin{array}{c}-CH-\\|\\CH_3\end{array}$ | 0 | 157–159 (Ethyl acetate-n-hexane) |
| 79 | H | F | Cl | H | H | $OCH_2H_5$ | $OC_2H_5$ | 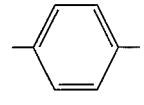 | $-O-$ | $-CH_2-$ | $-C_2H_4-$ | 1 | 197–199 (Ethanol-n-hexane) |
| 80 | H | F | Cl | H | H | $OCH_2H_5$ | $OC_2H_5$ | 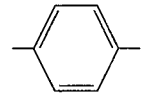 | $-O-$ | $-CH_2-$ | $-C_3H_6-$ | 1 | 193–195 (Ethanol-n-hexane) |
| 81 | H | F | H | H | H | $OC_2H_5$ | $\begin{array}{c}CH_3\\|\\O-CH\\|\\CH_3\end{array}$ | 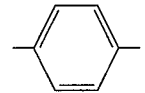 | $-O-$ | $-CH_2-$ | $-CH_2-$ | 0 | 152–155 (Ethyl acetate-n-hexane) |
| 82 | H | H | H | H | H | $OC_2H_5$ | $OC_2H_5$ | 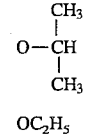 | Single bond | $-CH=CH-$ | $-C_3H_6-$ | 1 | 206–209 (Ethyl acetate-n-hexane) |

Example 83

Preparation of diethyl 4-[N-(8H-indeno[1,2-d]thiazol-2yl)sulfamoyl]benzylphosphonate Using the compound la obtained in Reference Example 1 and 4-[(diethoxyphosphoryl)methyl]benzenesulfonyl chloride, the procedure of Example 1 was otherwise repeated to provide the objective compound.

Melting point: 196°–198° C. (decomposition)(recrystallization solvent: methanol-chloroform-n-hexane)

Example 84

Preparation of diethyl 4-[N-(1-methyl-1H-naphtho[1,2-d]-imidazol-2-yl)carbamoyl]benzylphosphonate Using 2-amino-1-methyl-1H-naphtho[1,2-d]imidazole (commercially available) and 4-[(diethoxyphosphoryl)methyl] benzoyl chloride, the procedure of Example 1 was otherwise repeated to provide the objective compound.
Melting point: 173° C. (decomposition) (recrystallization solvent: chloroform-n-hexane)

Example 85

Preparation of diethyl 4-[N-(4H-indeno[2,1-d]thiazol-2yl)carbamoyl]benzylphosphonate Using 2-amino-4H-indeno[2,1-d]thiazol and 4[(diethoxyphosphoryl)methyl]benzoyl chloride, the procedure of Example 1 was otherwise repeated to provide the objective compound.
Melting point: 190° C. (decomposition) (recrystallization solvent: chloroform-n-hexane)

Example 86

Preparation of diethyl 4-[N-(7-chloro-8H-indeno[1,2-d]thiazol-2-yl)thiocarbamoyl]benzylphosphonate A 2.3 g portion of the compound obtained in Example 15 and 2.2 g of diphosphorus pentasulfide were suspended in a mixture of 20 ml of anhydrous pyridine and 20 ml of anhydrous benzene. The resulting suspension was refluxed with stirring for 10 hours. The reaction mixture was allowed to cool to room temperature, poured into ice water and extracted with chloroform. The chloroform layer was dried over anhydrous sodium sulfate and the solvent was distilled off under reduced pressure. The residue was subjected to silica gel column chromatography (eluent: chloroform-:methanol=60:1) and the crude crystals obtained were recrystallized from ethyl acetate-n-hexane to provide 0.5 g of the title compound as yellow crystals.
Melting point: 179.5°–180.5° C.

The compounds of the invention other than those described in the stated Examples include, for example:
diethyl 4-[N-(8H-indeno[1,2-d]thiazol-2-yl)thiocarbamoyl] benzylphosphonate
diethyl 4-[N-(4H-indeno[2,1-d]thiazol-2-yl)sulfamoyl]benzylphosphonate
diethyl 4-[N-(4H-indeno[2,1-d]thiazol-2-yl)thiocarbamoyl] benzylphosphonate
diethyl 4-[N-(6-chloro-8H-indeno[1,2-d]thiazol-2-yl)thiocarbamoyl]benzylphosphonate
diethyl 4-[N-(6-chloro-8H-indeno[1,2-d]thiazol-2-yl)sulfamoyl]benzylphosphonate
diethyl 4-[N-(8-fluoro-4H-[1]benzopyrano[4,3-d]- thiazol-2-yl)thiocarbamoyl] benzylphosphonate
diethyl 4-[N-(8-fluoro-4H-[1]benzopyrano[4,3-d]-thiazol-2-yl)sulfamoyl]benzylphosphonate
diethyl 4-[N-(1-methyl-1H-naphto[1,2-d]imidazol-2-yl)thiocarbamoyl]benzylphosphonate
diethyl 4-[N-(1-methyl-1H-naphto[1,2-d]imidazol-2-yl)sulfamoyl]benzylphosphonate
diethyl 3-{4-[N-(6-chloro-8H-indeno[1,2-d]thiazol-2-yl)carbamoyl]phenoxy} propylphosphonate
diethyl 3-{4-[N-(6-chloro-8H-indeno[1,2-d]thiazol-2-yl)thiocarbamoyl]phenoxy} propylphosphonate
diethyl 3-{4-[N-(6-chloro-8H-indeno[1,2-d]thiazol-2-yl) sulfamoyl]phenoxy} propylphosphonate
diethyl 2-{4-[N-(4H-indeno[2,1-d]thiazol-2-yl)carbamoyl] phenoxy}ethylphosphonate
diethyl 2-{4-[N-(4H-indeno[2,1-d]thiazol-2-yl)thiocarbamoyl]phenoxy}ethylphosphonate
diethyl 2-{4-[N-(4H-indeno[2,1-d]thiazol-2-yl)sulfamoyl] phenoxy}ethylphosphonate
diethyl 2-{4-[N-(8-fluoro-4H-[1]benzopyrano[4,3-d]thiazol-2-yl)thiocarbamoyl] phenoxy}ethylphosphonate
diethyl 2-{4-[N-(8-fluoro-4H-[1]benzopyrano[4,3-d]thiazol-2-yl)sulfamoyl]phenoxy }ethylphosphonate
diethyl 2-{4-[N-(1-methyl-1H-naphto[1,2-d]imidazol-2-yl) carbamoyl]phenoxy} ethylphosphonate
diethyl 2-{4-[N-(1-methyl-1H-naphto[1,2-d]imidazol-2-yl)thiocarbamoyl]phenoxy} ethylphosphonate
diethyl 2-{4-[N-(1-methyl-1H-naphto[1,2-d]imidazol-2-yl] sulfamoyl]phenoxy} ethylphosphonate
diethyl 4-[N-(4H-indeno[2,1-d]thiazol-2-yl)-N-methylcarbamoyl]benzylphosphonate
diethyl 4-[N-(8-fluoro-4H-[1]benzopyrano[4,3-d]thiazol-2-yl)-N-methylcarbamoyl] benzylphosphonate
diethyl 4-[N-(1-methyl-1H-naphto[1,2-d]imidazol-2-yl)-N-methylcarbamoyl]benzylphosphonate
diethyl 4-[N-(6-chloro-8H-indeno[1,2-d]thiazol-2-yl)-N-ethylthiocarbamoyl]benzylphosphonate
diethyl 4-[N-(6-chloro-8H-indeno[1,2-d]thiazol-2-yl)-N-ethylsulfamoyl]benzylphosphonate
diethyl 3-{4-[N-(6-chloro-8H-indeno[1,2-d]thiazol-2-yl)-N-ethylthiocarbamoyl]phenoxy} propylphosphonate
diethyl 3-{4-[N-(6-chloro-8H-indeno[1,2-d]thiazol-2-yl)-N-ethylsulfamoyl]phenoxy} propylphosphonate.

Pharmacological Test Example 1

Preventive and therapeutic effects of the compound of the invention on hyperlipidemia were determined using rats with Triton-induced hyperlipidemia according to the method of Kuroda et al. [Biochem. Biophys. Acta., 489, 119 (1977)] as follows.

Using 6 to 7-week-old male Wistar rats in groups of 5 (test groups), a solution of 300 mg/kg Triton (Triton WR 1339) in physiological saline was administered into the tail vein and, at the same time, 100 mg/kg of the test compound suspended in 0.5% CMC-Na solution was administered orally. As a control group, a group of 5 rats given Triton were orally dosed with 0.5% aqueous CMC-Na solution.

Twenty four hours after administration of Triton, blood was taken from the rats and the plasma total cholesterol and triglyceride were determined using Cholesterol C-Test Wako and Triglyceride G-Test Wako (both available from Wako Pure Chemical Industries, Ltd.) respectively. Using the measured values in the control group as references, the rates of decrease (%) in plasma total cholesterol and triglyceride in the test group were calculated by the following equation.

$$\text{Rate of decrease } (\%) = \left[ 1 - \frac{\text{(Test group value)}}{\text{(Control group value)}} \right] \times 100$$

The test rats were deprived of food before Triton administration through completion of blood sampling but allowed free access to drinking water.

Table 4 shows the results.

TABLE 4

| Test compound | Rate of decrease (%) | |
|---|---|---|
| (Example No.) | Total cholesterol | Triglyceride |
| 1 | 55 | 86 |
| 2 | 45 | 90 |
| 3 | 35 | 86 |
| 8 | 30 | 74 |
| 11 | 78 | 96 |
| 12 | 64 | 90 |
| 13 | 50 | 85 |
| 15 | 42 | 87 |
| 16 | 46 | 88 |
| 18 | 29 | 70 |
| 28 | 46 | 64 |
| 30 | 68 | 92 |
| 35 | 58 | 91 |
| 37 | 48 | 88 |
| 40 | 37 | 67 |
| 41 | 44 | 88 |
| 42 | 46 | 77 |
| 44 | 35 | 59 |
| 56 | 25 | 60 |
| 63 | 42 | 80 |
| 65 | 44 | 78 |
| 84 | 52 | 87 |

Formulation examples of the compound of the invention are described below.

Formulation Example 1 Manufacture of tablets

Using the compound obtained in Example 12 as an active ingredient, tablets (1000 tablets) each containing 250 mg of the active ingredient were manufactured according to the following formula.

| Ingredient | Amount (g) |
|---|---|
| Compound of Example 12 | 250 |
| Lactose (product of Japanese pharmacopeia: JP) | 33.5 |
| Corn starch (JP) | 16.5 |
| Carboxymethyl cellulose calcium (JP) | 12.5 |
| Methylcellulose (JP) | 6.0 |
| Magnesium stearate (JP) | 1.5 |
| Total | 320.0 |

According to the above formula, the compound of Example 12, lactose, corn starch and carboxymethyl cellulose calcium were well blended and granulated using an aqueous solution of methyl cellulose. The granulated mixture was passed through a 24-mesh sieve and the granules under the sieve were mixed with magnesium stearate and compression-molded into tablets.

Formulation Example 2 Manufacture of capsules

Using the compound obtained in Example 1 as an active ingredient, hard gelatin capsules (1000 units) each containing 250 mg of the active ingredient were manufactured according to the following formula.

| Ingredient | Amount (g) |
|---|---|
| Compound of Example 1 | 250 |
| Crystalline cellulose (JP) | 30 |
| Corn starch (JP) | 17 |
| Talc (JP) | 2 |
| Magnesium stearate (JP) | 1 |
| Total | 300 |

Thus, according to the above formula, the ingredients were finely divided and the powders obtained were blended to give a homogeneous composition. This composition was filled into proper-sized gelatin capsule shells for oral administration to provide the objective capsules.

Formulation Example 3 Manufacture of granules

Using the compound obtained in Example 30 as an active ingredient, granules (1000 g) containing 500 mg of the active ingredient in each gram were manufactured according to the following formula.

| Ingredient | Amount (g) |
|---|---|
| Compound of Example 30 | 500 |
| Crystalline cellulose (JP) | 100 |
| Corn starch (JP) | 250 |
| Lactose (JP) | 100 |
| Carboxymethyl cellulose calcium (JP) | 40 |
| Hydroxypropylmethyl cellulose (JP) | 10 |
| Total | 1000 |

Thus, according to the above formula, the compound of Example 30, lactose, corn starch, crystalline cellulose and carboxymethyl cellulose calcium were thoroughly blended and kneaded with an aqueous solution of hydroxypropyl cellulose. The resultant composition was granulated using an extrusion granulator and dried at 50° C. for 2 hours to provide the objective granules.

We claim:

1. A phosphonic diester derivative of the formula:

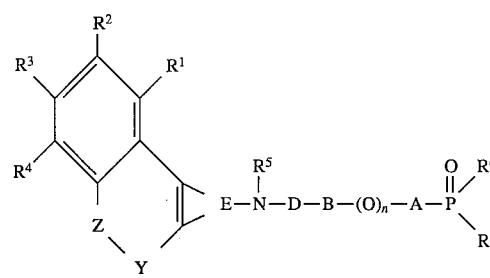

wherein $R^1$, $R^2$, $R^3$ and $R^4$ are the same or different and each represents a hydrogen atom, a lower alkyl group, a lower alkoxy group, a halogen-substituted lower alkyl group, a nitro group, a halogen atom, a cyano group, a phenylthio group, a phenylsulfinyl group, a phenylsulfonyl group, a phenyl(lower)alkoxy group, a phenyl(lower)alkylthio group or a benzoyloxy group having a di(lower alkoxy)phosphoryl(lower)alkyl group, and $R^3$ and $R^4$ may jointly represent a group of the formula —CH=CH—CH=CH—; $R^5$ represents a hydrogen atom, a lower alkyl group or a phenyl group; $R^6$ and $R^7$ are the same or different and each represents a lower alkoxy group, a phenyl group or a phenyl(lower)alkoxy group; A represents a lower alkylene group optionally having a phenyl group as a substituent; B represents a benzene ring or thiophene ring; D represents a group of the formula —CO—, —CS— or —SO$_2$—; E represents a group of the formula

a group of the formula

or a group of the formula

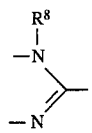

(wherein R$^8$ represents a lower alkyl group); —Z— represents a single bond or —O—; Y represents a lower alkylene group optionally having a phenyl group as a substituent or a vinylene group; and n is an integer of 0 or 1.

2. The phosphonic diester derivative as claimed in claim 1 wherein R$^1$, R$^2$, R$^3$ and R$^4$ in the formula (1) are the same or different and each represents a hydrogen atom, a lower alkyl group, a lower alkoxy group, a halogen-substituted lower alkyl group, a halogen atom or a cyano group; R$^5$ represents a hydrogen atom or a lower alkyl group; R$^6$ and R$^7$ each represent a lower alkoxy group; A represents a lower alkylene group; B represents a benzene ring; D represents a group of the formula —CO—; E represents a group of the formula

or a group of the formula

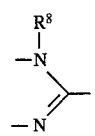

(wherein R$^8$ represents a lower alkyl group; —Z— represents a single bond or —O—; Y represents a lower alkylene group or a vinylene group; and n is 0.

3. The phosphonic diester derivative as claimed in claim 1 which is represented by the formula:

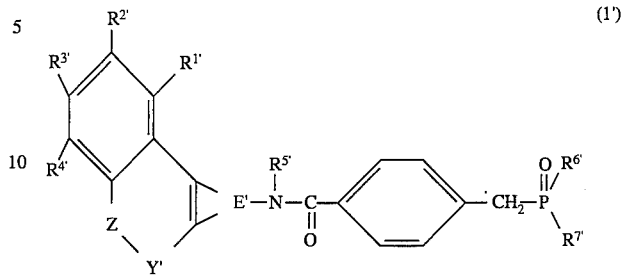

(1')

wherein R$^{1'}$, R$^{2'}$, R$^{3'}$ and R$^{4'}$ are the same or different and each represents a hydrogen atom, a lower alkyl group, a lower alkoxy group, a halogen-substituted lower alkyl group, a halogen atom or a cyano group; R$^{5'}$ represents a hydrogen atom or a lower alkyl group; R$^{6'}$ and R$^{7'}$ each represent a lower alkoxy group; E' represents a group of the formula

or a group of the formula

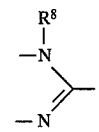

(wherein R$^8$ represents a lower alkyl group); —Z— is as defined above in claim 1; and Y' represents a lower alkylene group or a vinylene group.

4. The phosphonic diester derivative as claimed in claim 3 which is represented by the formula:

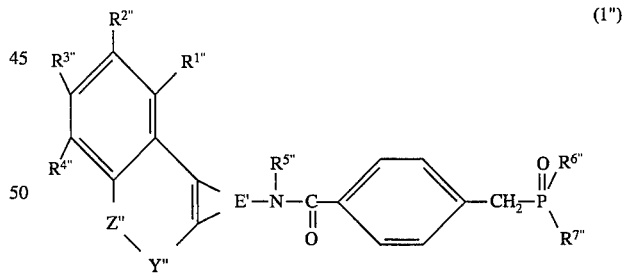

(1")

wherein R$^{1"}$, R$^{2"}$, R$^{3"}$ and R$^{4"}$ are the same or different and each represents a hydrogen atom, a lower alkyl group, a lower alkoxy group, a halogen-substituted lower alkyl group or a halogen atom; R$^{5"}$ represents a hydrogen atom or a lower alkyl group; R$^{6"}$ and R$^{7"}$ each represent a lower alkoxy group; E" represents a group of the formula

or a group of the formula

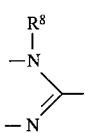

(wherein $R^8$ represents a lower alkyl group); when E" represents the group of

—Z"— represents a single bond or —O— and Y" represents a methylene group or a vinylene group, and when E" represents the group of

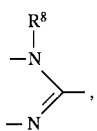

—Z"— represents a single bond and Y" represents a vinylene group.

5. The phosphonic diester derivative as claimed in claim 4 which is a compound selected from the group consisting of diethyl 4-[N-(8H-indeno[1,2-d]-thiazol-2-yl)carbamoyl] benzylphosphonate, diethyl 4-[N-6-chloro-8H-indeno[1,2-d]thiazol-2-yl)carbamoyl]benzylphosphonate, diethyl 4-[N-(7-chloro-8H-indeno-[1,2-d]-thiazol-2-yl)carbamoyl] benzylphosphonate, diethyl 4-[N(8-fluoro-4H-[1] benzopyrano[4,3-d]thiazol-2-yl)carbamoyl] benzylphosphonate, and diethyl 4-[N-(1-methyl-1H-naphtho[1,2-d]imidazol-2-yl)carbamoyl] benzylphosphonate.

6. The phosphonic diester derivative as claimed in claim 5 which is diethyl 4-[N-(6-chloro-8H-indeno[1,2-d]thiazol-2-yl)carbamoyl] benzylphosphonate.

7. An antihyperlipidemic composition comprising the phosphonic diester derivative claimed in any one of claims 1 to 6 as an active ingredient.

8. A method of treating hyperlipidemia which comprises administering to a patient a pharmacologically effective amount of the antihyperlipidemic composition claimed in claim 7.

* * * * *